(12) United States Patent
Hawkins et al.

(10) Patent No.: US 7,550,267 B2
(45) Date of Patent: Jun. 23, 2009

(54) MICROSCALE DIFFUSION IMMUNOASSAY UTILIZING MULTIVALENT REACTANTS

(75) Inventors: Kenneth R. Hawkins, Sammamish, WA (US); Paul Yager, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 11/226,054

(22) Filed: Sep. 14, 2005

(65) Prior Publication Data

US 2006/0166375 A1 Jul. 27, 2006

Related U.S. Application Data

(60) Provisional application No. 60/612,965, filed on Sep. 23, 2004.

(51) Int. Cl.
| | |
|---|---|
| *G01N 21/00* | (2006.01) |
| *G01N 31/00* | (2006.01) |
| *G01N 33/00* | (2006.01) |
| *G01N 33/53* | (2006.01) |
| *G01N 35/08* | (2006.01) |

(52) U.S. Cl. ............................. 435/7.1; 436/52; 436/53; 436/514; 436/518; 436/164; 436/172; 436/180; 422/81; 422/82; 422/82.08; 422/100

(58) Field of Classification Search .............. 424/136.1; 435/7.1, 286.5, 287.2, 288.5; 436/514, 536, 436/164

See application file for complete search history.

(56) References Cited

U.S. PATENT DOCUMENTS 3,449,938 A  6/1969  Giddings ....................... 73/23

(Continued)

FOREIGN PATENT DOCUMENTS

EP  0 294 701 B1  12/1988

(Continued)

OTHER PUBLICATIONS

Booker, H.E. et al, "Enzymatic Immunoassay vs. Gas/Liquid Chromatography for Determination of Phenobarbital and Diphenylhydantoin in Serum," *Clin. Chem.* 21:1766-1768, 1975.

(Continued)

*Primary Examiner*—Unsu Jung
(74) *Attorney, Agent, or Firm*—canady + lortz LLP; Karen S. Canady

(57) ABSTRACT

An improved microscale diffusion immunoassay utilizing multivalent reactants is disclosed. In particular, a method for detecting the presence of analyte particles in an analyte fluid is disclosed, the method comprising: (a) providing the analyte fluid comprising the analyte particles; (b) providing a diffusion fluid comprising binding particles capable of binding with the analyte particles; (c) flowing the analyte fluid and the diffusion fluid in adjacent laminar flow through a microfluidic channel; (d) allowing the analyte particles to diffuse into the diffusion fluid and bind with the binding particles to form analyte/binding particle complexes; and (e) detecting the presence of the analyte particles and the analyte/binding particle complexes, wherein each of the binding particles is capable of binding with more than one analyte particle, and wherein each of the analyte particles is capable of binding with more than one binding particle. Methods for determining the concentration of the analyte particles are also disclosed.

7 Claims, 8 Drawing Sheets

U.S. PATENT DOCUMENTS

| | | | |
|---|---|---|---|
| 3,795,489 A | 3/1974 | Warnick et al. | 23/254 R |
| 4,147,621 A | 4/1979 | Giddings | 210/22 C |
| 4,214,981 A | 7/1980 | Giddings | 209/155 |
| 4,250,026 A | 2/1981 | Giddings et al. | 209/155 |
| 4,683,212 A | 7/1987 | Uffenheimer | 436/52 |
| 4,726,929 A | 2/1988 | Gropper et al. | 422/68 |
| 4,737,268 A | 4/1988 | Giddings | 209/12 |
| 4,756,884 A | 7/1988 | Hillman et al. | 422/73 |
| 4,830,756 A | 5/1989 | Giddings | 210/739 |
| 4,849,340 A | 7/1989 | Oberhardt | 435/13 |
| 4,894,146 A | 1/1990 | Giddings | 209/12 |
| 4,908,112 A | 3/1990 | Pace | 204/299 |
| 5,007,732 A | 4/1991 | Ohki et al. | 356/70 |
| 5,039,426 A | 8/1991 | Giddings | 210/695 |
| 5,141,651 A | 8/1992 | Giddings | 210/748 |
| 5,156,039 A | 10/1992 | Giddings | 73/1 R |
| 5,193,688 A | 3/1993 | Giddings | 209/155 |
| 5,240,618 A | 8/1993 | Caldwell et al. | 210/748 |
| 5,250,263 A | 10/1993 | Manz | 422/81 |
| 5,288,463 A | 2/1994 | Chemelli | 422/68 |
| 5,304,487 A | 4/1994 | Wilding et al. | 435/291 |
| 5,389,524 A | 2/1995 | Larsen et al. | 435/29 |
| 5,439,578 A | 8/1995 | Dovichi et al. | 204/299 R |
| 5,465,849 A | 11/1995 | Wada et al. | 209/214 |
| 5,480,614 A | 1/1996 | Kamahori | 422/70 |
| 5,583,003 A * | 12/1996 | Hillyard et al. | 435/7.25 |
| 5,599,432 A | 2/1997 | Manz et al. | 204/451 |
| 5,599,503 A | 2/1997 | Manz et al. | 422/82.05 |
| 5,635,358 A | 6/1997 | Wilding et al. | 435/7.2 |
| 5,637,469 A | 6/1997 | Wilding et al. | 435/7.21 |
| 5,716,852 A * | 2/1998 | Yager et al. | 436/172 |
| 5,726,404 A | 3/1998 | Brody | 200/81 R |
| 5,726,751 A | 3/1998 | Altendorf et al. | 356/246 |
| 5,747,349 A | 5/1998 | van den Engh et al. | 436/172 |
| 5,748,827 A | 5/1998 | Holl et al. | 385/134 |
| 5,922,210 A | 7/1999 | Brody et al. | 210/767 |
| 5,932,100 A | 8/1999 | Yager et al. | 210/634 |
| 5,942,443 A | 8/1999 | Parce et al. | 436/514 |
| 5,948,684 A | 9/1999 | Weigl et al. | 436/52 |
| 5,971,158 A | 10/1999 | Yager et al. | 209/155 |
| 5,972,710 A | 10/1999 | Weigl et al. | 436/34 |
| 5,974,867 A | 11/1999 | Forster et al. | 73/61.41 |
| 6,067,157 A | 5/2000 | Altendorf | 356/337 |
| 6,136,272 A | 10/2000 | Weigl et al. | 422/82.05 |
| 6,221,677 B1 | 4/2001 | Wu et al. | 436/518 |
| 6,408,884 B1 | 6/2002 | Kamholz et al. | 137/827 |
| 6,482,306 B1 | 11/2002 | Yager et al. | 204/600 |
| 6,541,213 B1 | 4/2003 | Weigl et al. | 435/7.1 |
| 2002/0090644 A1 | 7/2002 | Weigl et al. | 435/7.1 |

FOREIGN PATENT DOCUMENTS

| | | |
|---|---|---|
| EP | 0 381 501 A2 | 8/1990 |
| EP | 0 645 169 A1 | 3/1995 |
| WO | WO 93/22053 | 11/1993 |
| WO | WO 96/04547 | 2/1996 |
| WO | WO 96/12541 | 5/1996 |
| WO | WO 96/15576 | 5/1996 |
| WO | WO 97/00125 | 1/1997 |
| WO | WO 97/02357 | 1/1997 |
| WO | WO 97/39338 | 10/1997 |
| WO | WO 98/43066 | 10/1998 |
| WO | WO 99/17100 | 4/1999 |
| WO | WO 99/17119 | 4/1999 |
| WO | WO 99/60397 | 11/1999 |

OTHER PUBLICATIONS

Brody et al., "Biotechnology at Low Reynolds Numbers," *Biophysical Journal* 71:3430-3441, Dec. 1996.

Brody, J.P. et al., "Diffusion-based extraction in a microfabricated device," *Sensors and Actuators A (Physical)* A58(1):13-18, 1997.

Brody, J.P. et al., "Low Reynolds Number Micro-Fluidic Device," *Solid State Sensor & Actuator Workshop*, Hilton Head, SC, pp. 105-108, Jun. 2-6, 1996.

Chiem, N. et al., "Microchip-Based Capillary Electrophoresis for Immunoassays: Analysis of Monoclonal Antibodies," *Anal. Chem.* 69:373-378, Feb. 1997.

Chmelík, Josef, "Isoelectric focusing field-flow fractionation," *J. Chromatography* 545(2) 349-358, 1991.

Darling et al., "Integration of microelectrodes with etched microchannels for in-stream electrochemical analysis," µTAS '98, Banff, Canada, pp. 105-108, Oct. 1998.

de Alwis et al., "Rapid Heterogeneous Competitive Electrochemical Immunoassay for IgG in the Picomole Range," *Anal. Chem.* 59:2786-2789, 1987.

Ekins, R., "Immunoassay: recent developments and future directions," *Nuclear Medicine and Biology* 21(3):495-521, 1994.

Faucheux, L. P. et al., "Optical Thermal Ratchet," *Phys. Rev. Letters* 74(9):1504-1507, Feb. 1995.

Fuh et al., "Rapid Diffusion Coefficient Measurements Using Analytical SPLITT Fractionation: Application to Proteins," *Anal. Biochem.* 208:80-87, 1993.

Giddings, J.C. et al. (1983), "Outlet Stream Splitting for Sample Concentration in Field-Flow Fractionation," *Separation Science & Technology* 18(3):293-306.

Giddings, J.C., "Field-Flow Fractionation: Analysis of Macromolecular, Colloidal and Particulate Materials," *Science* 260:1456-1465, Jun. 4, 1993.

Giddings, J.C., "Optimized Field-Flow Fractionation System Based on Dual Stream Splitters," *Anal. Chem.* 57(4):945-947, Apr. 1985.

Griffiths et al., "Human anti-self antibodies with high specificity from phage display libraries," *EMBO J.* 12(2):725-734, 1993.

Hatch, A. et al., "A rapid diffusion immunoassay in a T-sensor," *Nature Biotechnology* 19(5): 461-465, May 2001.

Hawkins, K.R. et al., "Diffusion immunoassay for protein analytes," in *2nd Annual International IEEE-EMBS Special Topic Conference on Microtechnologies in Medicine & Biology*, May 2-4, 2002, pp. 535-540.

Hawkins, K.R. et al., "The aggregation of multivalent immune complexes expands the useful analyte size range of the diffusion immunoassay," *Micro Total Analysis Systems 2004*, vol. 1, Royal Society of Chemistry, Cambridge, U.K., 2004, pp. 129-131.

Hicks, J.M., "Fluorescence Immunoassay," *Human Pathology* 15(2):112-116, Feb. 1984.

Kamholz et al., "Quantitative Analysis of Molecular Interaction in a Microfluidic Channel: The T-Sensor," *Anal. Chem.* 71(23):5340-5347, Dec. 1999.

Leff, H.S. et al., "Resource letter MD-1: Maxwell's demon," *Am. J. Physics* 58(3):201-209, 1990.

Manz, A. et al., "Planar chips technology for miniaturization of separation systems: A developing perspective in chemical monitoring," *Advances in Chromatography* 33:2-66, 1993.

McGregor et al., "Polarisation Fluoroimmunoassay of Phenytoin," *Clin. Chim. Acta* 83:161-166, 1978.

Montgomery et al., "Determination of Diphenylhydantoin in Human Serum by Spin Immunoassay," *Clin. Chem.* 21(2):221-226, 1975.

Paxton, J.W. et al., "Production and Characterisation of Antisera to Diphenylhydantoin Suitable for Radioimmunoassay," *J. Immunol. Methods* 10:317-327, 1976.

Petersen, K.E., "Silicon as a Mechanical Material," *Proc. IEEE* 70(5):420-457, May 1982.

Porstmann, T. et al., "Enzyme immunoassay techniques," *J. Immunol. Methods* 150:5-21, 1992.

Reisman, A. et al., "The Controlled Etching of Silicon in Catalyzed Ethylenediamine-Pyrocatechol-Water Solutions," *J. Electrochem. Soc.* 126(8):1406-1415, Aug. 1979.

Rousselet, J. et al., "Directional motion of brownian particles induced by a periodic asymmetric potential," *Nature* 370:446-448, Aug. 11, 1994.

Shoji, S. et al., "Microflow devices and systems," *J. Micromechanics and Microengineering* 4:157-171, 1994.

Verpoorte, E.M.J. et al., "Three-dimensional micro flow manifolds for miniaturized chemical analysis systems," *J. Micromech. Microeng.* 4:246-256, 1994.

Wallis, G. et al., "Field Assisted Glass-Metal Sealing," *J. Appl. Physics* 40(10):3946-3949, Sep. 1969.

Weigl et al., "Diffusion-Based Optical Chemical Detection in Silicon Flow Structures," *Anal. Methods & Instrumentation. Special Issue µTAS '96*, Nov. 1996, pp. 174-184.

Weigl et al., "Simultaneous self-referencing analyte determination in complex sample solutions using microfabricated flow structures (T-Sensors)," *µTAS '98*, Banff, Canada, Oct. 1998.

Weigl, B.H. et al. (Feb. 1997), "Fluorescence and absorbance analyte sensing in whole blood and plasma based on diffusion separation in silicon-microfabricated flow structures," SPIE Proceedings, J. Lakowitz (ed.), *Fluorescence Sensing Technology III* (Feb. 9-11), pp. 171-181.

Weigl, B.H. et al. (Nov. 1996), "Rapid sequential chemical analysis in microfabricated flow structures using multiple fluorescent reporter beads," *Analytical Methods & Instrumentation. Special Issue µTAS 96*, p. 255.

Weigl, B.H. et al., "Microfluidic Diffusion-Based Separation and Detection," *Science* 283:346-347, Jan. 1999.

Weigl, B.H. et al., "Silicon-microfabricated diffusion-based optical chemical sensor," *Sensors and Actuators B (Chemical)* B39 (1-3), 452-457, Mar./Apr. 1996.

Williams, P.S. et al., "Continuous SPLITT Fractionation Based on a Diffusion Mechanism," *Ind. Eng. Chem. Res.* 31:2172-2181, 1992.

\* cited by examiner

MICROSCALE DIFFUSION IMMUNOASSAY UTILIZING MULTIVALENT REACTANTS

CROSS-REFERENCE TO RELATED APPLICATION

This application claims the benefit under 35 U.S.C. § 119 (e) of U.S. Provisional Patent Application No. 60/612,965 filed Sep. 23, 2004, which provisional application is incorporated herein by reference in its entirety.

STATEMENT OF GOVERNMENT INTEREST

This invention was made with government support under Grant No. 8R01EB002023-03 awarded by the National Institutes of Health. The government has certain rights in this invention.

BACKGROUND OF THE INVENTION

1. Field of the Invention

The present invention relates to immunoassays, and, more particularly, to improved microscale diffusion immunoassays utilizing multivalent reactants.

2. Description of the Related Art

The immunoassay is the workhorse of analytical biochemistry. It allows the unique binding abilities of antibodies to be widely used in selective and sensitive measurement of small and large molecular analytes in complex samples. The driving force behind developing new immunological assays is the constant need for simpler, more rapid, and less expensive ways to analyze the components of complex sample mixtures. Current uses of immunoassays include therapeutic drug monitoring, screening for disease or infection with molecular markers, screening for toxic substances and illicit drugs, and monitoring for environmental contaminants.

Flow injection immunoassays have taken advantage of specific flow conditions (see U. de Alwis and G. S. Wilson, *Anal. Chem.* 59, 2786-9 (1987)), but also use high Reynolds number effects for mixing. Micro-fabricated capillary electrophoresis devices, which are truly microfluidic, have been used for rapidly separating very small volumes of immunoreagents following binding reactions (see N. Chiem and D. J. Harrison, *Anal. Chem.* 69,373-8 (1997)). However, one of the unique features of microfluidic devices that has yet to be fully exploited for immunoassay development is the presence of laminar flow under low Reynolds number conditions. Laminar flow allows for quantitative diffusional transport between adjacent flowing streams, while retaining the relative positions of essentially non-diffusing components such as cells and larger microspheres. While these conditions are impediments to the application of some macro-scale techniques, they allow for the creation of new types of analyses that are uniquely well suited to microfluidic systems, such as the H-Filter for extraction of solutes (see J. P. Brody, P. Yager, R. E. Goldstein and R. H. Austin, *Biophysical Journal* 71(6), 3430-3441 (1996); U.S. Pat. No. 5,932,100; and J. P. Brody and P. Yager, *Sensors and Actuators A (Physical)* A58(1), 13-18 (1997)), the V-Groove device for low-volume flow cytometry (see U.S. Pat. No. 5,726,751), the T-Sensor for detection of diffusable analytes (see A. E. Kamholz, B. H. Weigl, B. A. Finlayson and P. Yager, *Anal. Chem.* 71(23), 5340-5347 (1999); U.S. Pat. No. 5,716,852; U.S. Pat. No. 5,972,710; B. H. Weigl and P. Yager, *Science* 283, 346-347 (1999); R. B. Darling, J. Kriebel, K. J. Mayes, B. H. Weigl and P. Yager, Integration of microelectrodes with etched microchannels for in-stream electrochemical analysis, μTAS '98, Banff, Canada (1998); B. H. Weigl and P. Yager, *Sensors and Actuators B (Chemical)* B39 (1-3), 452-457 (1996); B. H. Weigl, M. A. Holl, D. Schutte, J. P. Brody and P. Yager, *Anal. Methods & Instr.* 174-184 (1996); and B. H. Weigl et al., Simultaneous self-referencing analyte determination in complex sample solutions using microfabricated flow structures (T-Sensors), μTAS '98, Banff, Canada (1998)); and others as described in U.S. Pat. No. 5,922,210; U.S. Pat. No. 5,747,349; U.S. Pat. No. 5,748,827; U.S. Pat. No. 5,726,404; U.S. Pat. No. 5,971,158; U.S. Pat. No. 5,974,867; U.S. Pat. No. 5,948,684; WO 98/43066, published Oct. 1, 1998; U.S. patent application Ser. No. 08/938,584, filed Sep. 26, 1997; WO 99/17100, published Apr. 8, 1999; WO 99/17119, published Apr. 8, 1999; U.S. patent application Ser. No. 09/196,473, filed Nov. 19, 1998; U.S. patent application Ser. No. 09/169,533, filed Oct. 9, 1998; WO 99/60397, published Nov. 25, 1999; U.S. patent application Ser. No. 09/404,454, filed Sep. 22, 1999; and U.S. patent application Ser. No. 09/464,379, filed Dec. 15, 1999.

A number of microscale diffusion immunoassays (DIAs) were disclosed in U.S. Pat. No. 6,541,213 ("the '213 patent"), which patent is incorporated herein by reference in its entirety. As described therein, such DIAs may be utilized to determine the presence and concentration of an analyte in an analyte fluid by: flowing the analyte fluid, comprising analyte particles, and a diffusion fluid, comprising binding particles (such as antibodies), in adjacent laminar flow in a microfluidic laminar flow channel; allowing the analyte particles to diffuse into the diffusion fluid and bind with the binding particles to form analyte/binding particle complexes; and detecting the presence of said analyte particles, both complexed and uncomplexed. As further noted in the '213 patent, such a DIA relies on the change in the transport properties of the analyte when it becomes complexed with a binding particle (i.e., the diffusion profile of the analyte is modified by the binding particle). In particular, it is noted that the analyte/binding particle complexes diffuse more slowly than the analyte in its unbound state, and, therefore, a population of such complexes will accumulate near the diffusion interface between the two fluid streams. By monitoring the diffusion profile of the analyte (both bound in a complex and unbound) for any changes, the binding event can be detected without the need for separation of the analyte/binding particle complexes from the original populations of analyte and binding particles and without the requirement that the properties of the analyte particles change with binding.

However, in order for changes in the diffusion profile of the analyte to be detectable in the foregoing DIA, the analyte/binding particle complexes must have significantly different diffusion properties than the unbound analyte particles. For example, as noted in the '213 patent, the ratio of diffusivity of the complexes to the diffusivity of the unbound analyte particles should be greater than about two in order for the DIA response to be resolvable from the experimental noise levels typical for the DIA. This creates a limit on the size of the analyte particles depending on the size of the binding particles. For example, if the binding particles are antibodies (MW ~150 kD), then the analyte particles cannot exceed ~45 kD. To detect a larger analyte, the binding particles must be correspondingly larger, such as an antibody immobilized on the surface of a microsphere (see K. R. Hawkins, A. Hatch, H. Chang and P. Yager, "Diffusion Immunoassay of Protein Analytes," 2$^{nd}$ *Annual International Conference IEEE-EMBS Special Topic Conference on Microtechnologies in Medicine and Biology*, May 2-4, 2002, Madison, Wis., USA, 2002).

Accordingly, although there have been advances in the field, there remains a need in the art for new and improved microscale diffusion immunoassays, in particular, DIAs having increased response sensitivity, which are not subject to the above limitations. The present invention addresses these needs and provides further related advantages.

BRIEF SUMMARY OF THE INVENTION

In brief, the present invention is directed to improved microscale diffusion immunoassays utilizing multivalent reactants. As described herein, by utilizing multivalent reactants (i.e., analyte and binding particles) in the microscale diffusion immunoassays disclosed in the '213 patent, a number of the limitations of such assays noted above may be overcome. In particular, the use of multivalent reactants enables the detection of larger analyte particles.

In one embodiment, a method for detecting the presence of analyte particles in an analyte fluid is provided, the method comprising: (a) providing the analyte fluid comprising the analyte particles; (b) providing a diffusion fluid comprising binding particles capable of binding with the analyte particles; (c) flowing the analyte fluid and the diffusion fluid in adjacent laminar flow through a microfluidic channel; (d) allowing the analyte particles to diffuse into the diffusion fluid and bind with the binding particles to form analyte/binding particle complexes; and (e) detecting the presence of the analyte particles and the analyte/binding particle complexes, wherein each of the binding particles is capable of binding with more than one analyte particle, and wherein each of the analyte particles is capable of binding with more than one binding particle.

In a further embodiment, the method further comprises: detecting a diffusion profile in the microfluidic channel formed by the analyte particles and the analyte/binding particle complexes; and determining the concentration of the analyte particles. In more specific embodiments, the concentration of analyte particles may be determined based upon the diffusion profile of the analyte particles and analyte/binding particle complexes, or by comparing the diffusion profile to a calibration profile.

As in the '213 patent, in the DIAs of the present invention, the binding particles, the analyte particles, and/or the analyte/binding particle complexes must be visible or detectable, e.g., by optical or electrical detection means or other detection means known to the art, or must be labeled to become visible or detectable. Accordingly, in further embodiments, at least one of the analyte particles is labeled with a detectable marker and/or at least one of the binding particles is labeled with a detectable marker.

These and other aspects of the invention will be evident upon reference to the attached figures and following detailed description.

BRIEF DESCRIPTION OF THE SEVERAL VIEWS OF THE DRAWINGS

FIG. 1A shows initial conditions in an interdiffusion competition assay. Two volumes of fluid are placed into interdiffusive contact. One fluid contains a high molecular weight binding particle, such as specific antibody (Ab) (left side). The other fluid (right side) contains at least one labeled (label shown by square-shaped particles) conjugate of the analyte particle (e.g., antigen) to be monitored (LA), as well as unlabeled analyte particles (e.g., sample antigen) (SA) (irregular particles). FIG. 1B is a schematic representation of the concentration of LA across the diffusion dimension at an early stage of diffusion (free (LA), antibody-bound (AbLA), and total (LA+AbLA)). Here, the initial concentrations of Ab are much greater than LA+SA, allowing a significant fraction of LA and SA to bind. FIG. 1C is a schematic representation of the case when Ab is much less than LA+SA. A small fraction of antigen molecules are able to bind due to the saturation of binding sites resulting in a diffusion profile more similar to that of free diffusion. Less LA accumulates near the fluid interface.

FIG. 2 depicts a T-sensor apparatus for conducting a diffusion immunoassay in a T-Sensor.

FIG. 3 shows data comparing the predicted and actual observations of a diffusion immunoassay of the present invention.

DETAILED DESCRIPTION OF THE INVENTION

Figure 1:
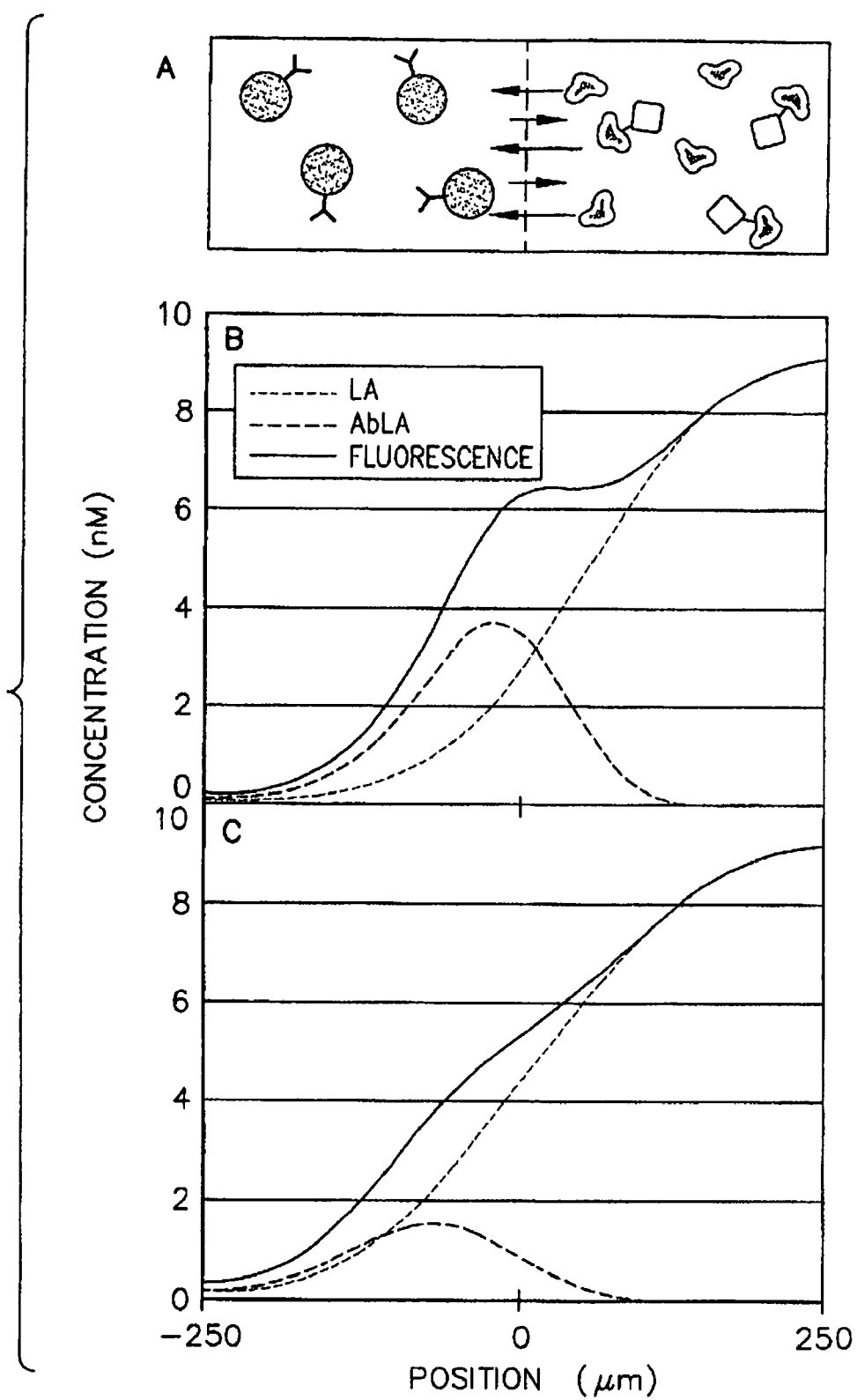
FIG. 1 is a schematic representation of a representative microscale diffusion immunoassay disclosed in the '213 patent.

As noted above, the present invention is directed to improved microscale diffusion immunoassays (DIAs) utilizing multivalent reactants. For example, in one embodiment, a method for detecting the presence of analyte particles in an analyte fluid is provided, the method comprising: (a) providing the analyte fluid comprising the analyte particles; (b) providing a diffusion fluid comprising binding particles capable of binding with the analyte particles; (c) flowing the analyte fluid and the diffusion fluid in adjacent laminar flow through a microfluidic channel; (d) allowing the analyte particles to diffuse into the diffusion fluid and bind with the binding particles to form analyte/binding particle complexes; and (e) detecting the presence of the analyte particles and the analyte/binding particle complexes, wherein each of the binding particles is capable of binding with more than one analyte particle, and wherein each of the analyte particles is capable of binding with more than one binding particle.

More specifically, the binding particles employed in the DIA of the present invention have more than one binding site, and such binding sites are spatially separated by a sufficient distance such that the binding of an analyte particle at one site does not inhibit the binding of another analyte particle at a second site. Similarly, the analyte particles employed in the DIA of the present invention have more than one binding site, and such binding sites are spatially separated by a sufficient distance such that the binding of a binding particle at one site does not inhibit the binding of another binding particle at a second site. As one of skill in the art will appreciate, the binding sites of the binding and analyte particles are sufficiently similar to each have a high binding affinity with the analyte and binding particles, respectively, but are not necessarily the identical.

By using multivalent reactants (i.e., analyte and binding particles capable of binding with more than one binding and analyte particle, respectively), the DIAs of the present invention enable cross-linking between the resulting analyte/binding particle complexes. Provided that the diffusion coefficients of these cross-linked aggregates are greater than that of the analyte particles by an amount sufficient for the DIA response to be resolvable from typical experimental noise levels (e.g., about two times greater, as noted in the '213 patent), the DIAs of the present invention allows for the diffusion coefficient of the non-aggregated complexes to be essentially the same as that of the analyte particles. This expands the list of possible analytes to include classes of molecules which were not amenable to analysis by the DIA disclosed in the '213 patent without embellishments to the basic technique disclosed therein, such as the immobilization of the binding particles onto microspheres.

For example, in a specific embodiment, each of the binding particles is an antibody and each of the analyte particles has more than one copy of the corresponding epitope spatially separated such that the binding of an antibody to one epitope does not sterically hinder the binding of a second antibody to another. Other possible multivalent reactants include, but are not limited to, the binding and analyte particles listed in the following Table 1.

TABLE 1

| Analyte Particles | Binding Particles |
|---|---|
| Multimeric proteins* | Antibodies |
| Small molecule multimers** | F(ab)'$_2$ antibody fragments |
| | Antibody decorated microspheres |
| | High-affinity molecularly-templated microspheres |

*provided that the recognition sites are not uniquely located at a multimer interface
**provided that the recognition site is in the repeated unit As in the '213 patent, in the DIA of the present invention, the binding particles, the analyte particles, and/or the analyte/binding particle complexes must be visible or detectable, e.g., by optical or electrical detection means or other detection means known to the art, or must be labeled to become visible or detectable. Accordingly, in further embodiments, at least one of the analyte particles is labeled with a detectable marker and/or at least one of the binding particles is labeled with a detectable marker.

As noted above, the DIAs of the present invention may be utilized to determine the concentration of the analyte particles by detecting a diffusion profile in the microfluidic channel formed by the analyte particles and the analyte/binding particle complexes, and determining the concentration of the analyte particles. The concentration of the analyte particles may be determined based upon the diffusion profile of the analyte particles and analyte/binding particle complexes, or by comparing the diffusion profile to a calibration profile.

As used herein, the terminology "diffusion front" (or "diffusion profile") refers to a detectable edge or line created by diffusing particles. It may be more or less sharp or diffuse depending on system parameters such as relative amounts of analyte and binding particles, relative diffusion coefficients of both, amount of labeling, viscosities of the system, and other parameters known to the art. The term "slowing" with reference to the diffusion front includes stopping, as well as any detectable amount of slowing. The "diffusion front" may include a detectably more intense area or line closer to the point(s) from which diffusion of particles begins caused by complexing of labeled particles to form slower-diffusing complexes, with relatively less intense areas further from said points caused by uncomplexed labeled particles; or the "diffusion front" may be the absolute border of the area into which particles have diffused.

In general, as noted in the '213 patent, systems allowing diffusion of analyte or binding particles toward each other can be systems in which fluids containing analyte particles (referred to herein as "analyte fluids") are placed in contact with fluids containing binding particles (referred to herein as "diffusion fluids"), or fluids containing analyte particles, are placed in contact with solids containing binding particles capable of diffusing into the analyte fluid. Or, the system may be one in which fluids containing binding particles are placed in contact with solids containing analyte particles capable of diffusing into the diffusion fluids. Such systems can be flowing or stationary systems, or can comprise fluids separated by membranes capable of allowing diffusion of analyte and/or binding particles therethrough, or can comprise two fluids containing analyte and binding particles respectively separated by a removable barrier, which is removed to allow diffusion to take place.

Slowing of the diffusion front may be observed or detected; or the position of the diffusion front after a predetermined time from when the particles begin diffusing may be observed or otherwise detected and compared with a similar calibration or control system or systems containing known amounts of analyte particles, e.g., from 0 to any typical concentration. In this way, concentration as well as presence of analyte particles can be determined. The concentration of analyte particles may also be calculated based on the principles and algorithms described in the '213 patent, and without undue experimentation by those skilled in the art.

In certain embodiments of the analytical methods of this invention, analyte particles in the system may be supplemented with labeled analyte particles, and the diffusion front observed and compared with systems containing only labeled analyte particles (and no unlabeled analyte particles). Earlier and more complete slowing or stopping of the diffusion front will occur when (as a result of complexation of analyte particles with binding particles) the concentration of binding particles more greatly exceeds that of the analyte particles. However, it is not essential that binding particle concentration exceed analyte particle concentration.

Detectable markers or labeling agents for labeling the analyte particles or binding particles include any particles capable of binding or adhering thereto and not interfering with binding of the analyte and binding particles selected for the assay. Labeling agents may include fluorescent, phosphorescent, chemiluminescent, enzyme particles, and other labeling agents known to the art. The terms "labeled antigen" and "LA" as used herein refer to labeled analyte particles. Labeling agents should be small enough to provide label/analyte particle complexes which are of similar size (at least in the same order of magnitude) as the unlabeled analyte particles so that diffusion coefficients of the labeled analyte particles are roughly equivalent to diffusion coefficients of unlabeled analyte particles. For example, an analyte particle having a molecular weight of 10,000 might be labeled with a molecule having a molecular weight of about 100 to 1,000. The labeling particle should not be so large as to significantly change the diffusion properties of the binding particle/labeled analyte complex as compared to the diffusion properties of the binding particle analyte complex. The label may be soluble or insoluble in the fluid and may adhere to the analyte particle by adsorption, absorption or chemical binding. For example, the labeling agent can be a conventional art-known dye, a metal particle, or any other detectable particle known to the art.

The term "particles" includes molecules, cells, large molecules such as proteins, small molecules comprised of one or several atoms, and ions. The particles may be suspended or dissolved in the fluid streams. The term "stream" refers to a carrier fluid such as water or other liquid, air or other gas, dissolving or suspending the particles. The term "particles" as used herein does not include the molecules of the carrier stream.

The binding particle may be any particle capable of binding or adhering to the analyte particle and with the labeled analyte particle; e.g., by covalent or ionic binding, absorption, adsorption, or other means known to the art. The binding particle may be an antibody, either monoclonal or polyclonal, or a synthetic binding particle made using a combinatorial or molecular-imprinting process to provide a specific binding site, or a particle of a substance such as activated charcoal capable of adhering to the labeled analyte particle. Binding particles as defined above may also function as analyte particles; e.g., antibodies may function as analyte particles herein. Preferably the binding particle has a binding affinity to the analyte particle of at least about $10^7$ $M^{-1}$ to about $10^{10}$ $M^{-1}$ and more preferably at least about $10^8$ $M^{-1}$. Since antibodies typify a preferred class of binding particles of this invention, the terms "antibody" or "AB" as used herein also refer to "binding particles."

The diffusion fluid is a carrier fluid for the binding particles and can be any carrier fluid having a viscosity which allows diffusion of the analyte particles into the diffusion stream. In some systems, the viscosity of the diffusion fluid is between about one and about four times that of water. More viscous systems require longer times for performing the assay. The viscosities of the analyte fluid and the diffusion fluid need not be the same and can differ greatly so long as diffusion from the analyte fluid into the diffusion fluid is significant enough to allow measurement. The diffusion fluid is capable of dissolving or suspending the binding particles and the analyte particles at the flow rate used to flow the diffusion stream through the laminar flow or microfluidic channel.

The term "laminar flow" of two streams means stable, side-by-side, non-recirculating, flow of two streams without mixing. There are no zones of recirculation, and turbulence is negligible. A "laminar flow channel" or "microfluidic channel" is a channel having dimensions, as is known to the art, allowing such non-turbulent flow under flow rates used.

As is known to the art, a field force may be exerted in the diffusion direction of the fluids to enhance the effects of diffusion and the signal to noise ratio of the detection means chosen. Such field forces include magnetic, gravitational, and electrical fields.

Certain embodiments of the methods of this invention are designed to be carried out in devices comprising microchannels of a size such that the Reynolds number for flow within the channel is below about 1. Reynolds number is the ratio of inertial effects to viscous effects in a given flow stream. Low Reynolds number means that inertia is essentially negligible, turbulence is essentially negligible, and the flow of the two adjacent streams is laminar; i.e., the streams do not mix except for the diffusion of particles as described above.

Figure 2A:
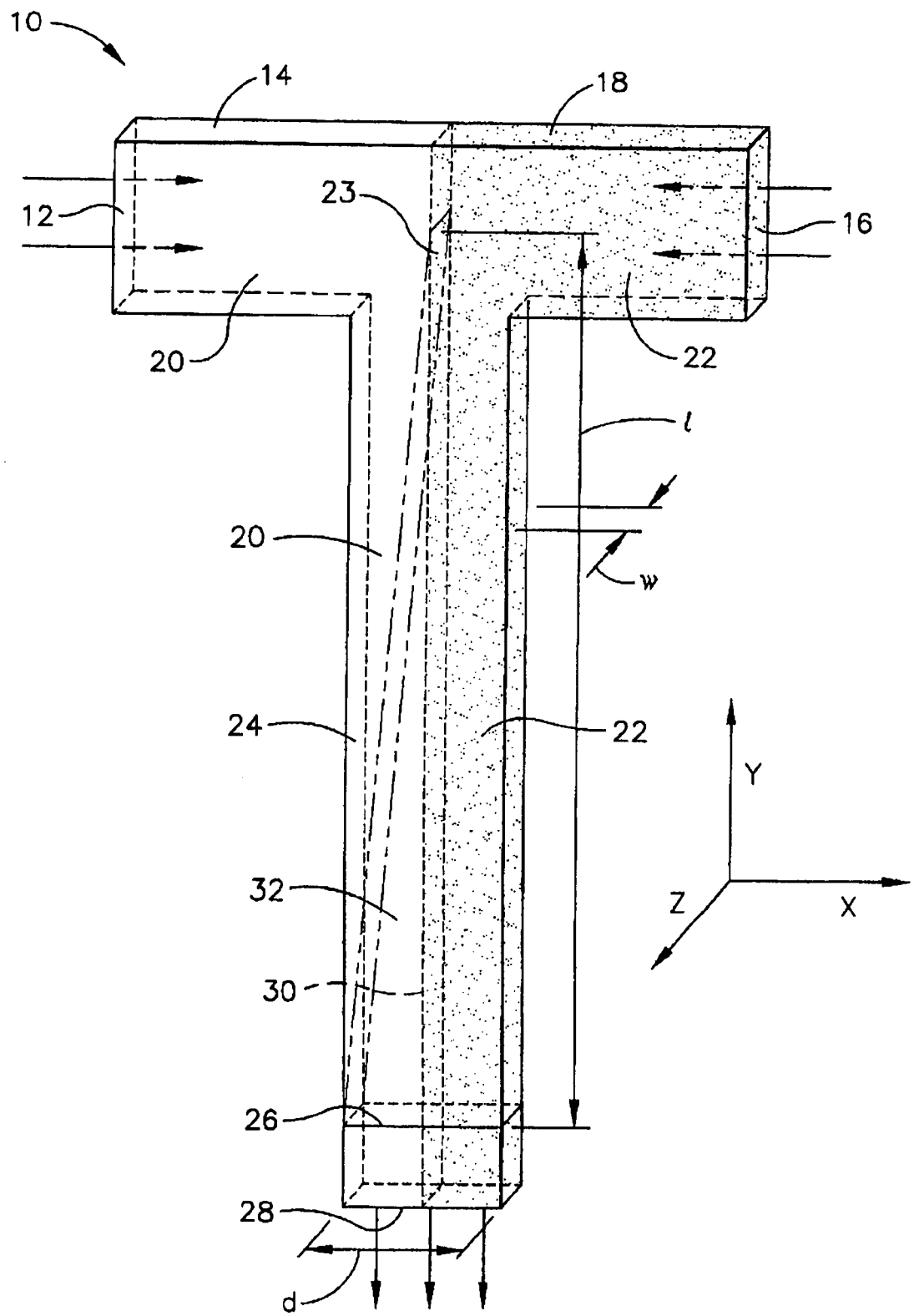
FIG. 2A is a schematic illustration showing diffusion of antibody (AB) (left side), and labeled antigen (LA) (right side).

The distance in the flow direction of the laminar flow channel from the entrance of the channel to the detection area is called its length (l). Referring to FIG. 2A, l is measured from the middle of analyte stream inlet 16 to detection zone 26. The channel dimension in the direction of particle diffusion at right angles to the length (l) is called its depth (d). The third channel dimension at right angles to both the length and depth is called its width (w). The depth (d) is therefore perpendicular to the plane of interface of the analyte and diffusion streams.

The laminar flow channel may include inlets and outlets along its length to provide reference or other reagent streams, or conduct separate streams away from the channel for analysis, disposal, or further processing. The devices of this invention may also include inlets for reference and control streams as described in U.S. Pat. No. 5,948,684.

The analyte stream inlet and the diffusion stream inlet need only be sized large enough to conduct the analyte and diffusion streams into parallel laminar flow; e.g., may comprise channels less than or equal to about 5 mm in length, less than about 100 micrometers in depth and less than or equal to about 5 mm in width, preferably less than about 1 mm in width. These inlets may be as long, deep and wide as required by the system of which they are a part, however, they preferably have a volume less than about 2.5 microliters to accommodate small sample sizes.

The width and depth of the laminar flow channel and inlet and outlet channels must be large enough to allow passage of the particles and is preferably between about 3 to 5 times the diameter of any particles present in the streams and less than or equal to 5 mm. The width is preferably less than or equal to 1 mm.

Means for injecting the analyte and diffusion streams into the device are provided, and include standard syringes and tubes. Means for removing fluid from the outlet(s) may also be provided, including receptacles for the fluid, inducing flow by capillary attraction, pressure, gravity, and other means known to the art as described above. Such receptacles may be part of an analytical or other device for further processing the streams or portions thereof.

The detectable diffusion profile of the flowing microchannel embodiments of this invention is the spatial location of labeled analyte particles within the reference area. The diffusion profile for a given concentration of analyte particles stays the same over time in these systems as long as the flow speed is constant, when dynamic equilibrium has been reached. The diffusion profile can be varied by varying flow rate, analyte concentration, and/or binding particle concentration so as to optimize the signal for detection.

The detection area is the portion of the laminar flow channel where the diffusion profile is interrogated by the detection means. It should be far enough from the junction of the two streams for significant reaction between binding particles and analyte particles to have occurred. However, it should not be so far along the channel that the particles have spread apart enough to significantly diminish signal intensity. The detection area, i.e., the length (l) from the junction of the analyte and diffusion fluids to the point where the diffusion profile is detected, can be optimized in accordance with these principles to optimize signal-to-noise ratio.

The step of allowing the particles to diffuse includes allowing the analyte and diffusion streams to be in contact for a sufficient period of time to form a stable diffusion profile at the detection area.

The length of the laminar flow channel is long enough to permit small analyte particles and labeled analyte particles to diffuse from the analyte stream and bind to the binding particles and can vary from several microns to 50 mm or more, depending on the sensitivity and size of the detection means, the pump capacities and flow rates and volumes, and diffusion of the particles. Flow rates may be adjusted to be fast enough to prevent particles from settling. Flow rates can vary as required; e.g., between about 5 μm/sec to about 5000 μm/sec.

As further described in the '213 patent, the methods of this invention may be performed using reference and/or control streams in laminar flow in the laminar flow channel with the analyte and diffusion streams. For example, a reference stream containing a known concentration of analyte particles and labeled analyte particles may be flowed into the laminar flow channel adjacent to the diffusion stream so that the diffusion profile of the analyte stream into the diffusion stream may be directly compared with the diffusion profile of the reference stream into the diffusion stream.

The term "microfabricated" refers to devices having dimensions such that flow therein is substantially laminar. Preferably the width (dimension orthogonal to the diffusion direction and the flow direction) of the channels is less than about 1 mm.

The devices of this invention can be fabricated from any moldable, machinable or etchable material such as glass, plastic, or silicon wafers. Substrate materials which are optically transparent for a given wavelength range allow for optical detection in that wavelength range, e.g., absorbance or fluorescence measurements, by transmission. Alternatively, substrate materials which are reflective allow for optical detection by reflection. Substrate materials do not have to allow for optical detection because other art-known methods of detection are suitable as well. Non-optical detection methods include electrochemical detection and conductivity detection.

The term "machining" as used herein includes printing, stamping, cutting and laser ablating. The devices can be formed in a single sheet, in a pair of sheets sandwiched together, or in a plurality of sheets laminated together. The term "sheet" refers to any solid substrate, flexible or otherwise. The channels can be etched in a silicon substrate and covered with a cover sheet, which can be a transparent cover sheet. In a laminated embodiment, the channel walls are defined by removing material from a first sheet and the channel top and bottom are defined by laminating second and third sheets on either side of the first sheet. Any of the layers can contain fluid channels. In some cases the channel is simply a hole (or fluid via) to route the fluid to the next fluid laminate layer. Any two adjacent laminate layers may be permanently bonded together to form a more complex single part. Often fluidic elements that have been illustrated in two separate layers can be formed in a single layer.

Each layer of a laminate assembly can be formed of a different material. The layers are preferably fabricated from substantially rigid materials. A substantially rigid material is inelastic, preferably having a modulus of elasticity less than 1,000,000 psi, and more preferably less than 600,000 psi. Substantially rigid materials can still exhibit dramatic flexibility when produced in thin films. Examples of substantially rigid plastics include cellulose acetate, polycarbonate, methylmethacrylate and polyester. Metals and metal alloys are also substantially rigid (examples include steels, aluminum, copper, etc. . . . ). Glasses, silicon and ceramics are also substantially rigid.

To create the fluidic element in the sheets, material may be removed to define the desired structure. The sheets can be machined using a laser to ablate the material from the channels. The material can be removed by traditional die cutting methods. For some materials chemical etching can be used. Alternatively, the negative of the structure desired can be manufactured as a mold and the structure can be produced by injection molding, vacuum thermoforming, pressure-assisted thermoforming or coining techniques.

The individual layers, assemblies of layers, or molded equivalents may be bonded together using adhesives or welding. Alternatively, the layers may be self-sealing or mechanical compression through the use of fasteners such as screws, rivets and snap-together assembly can be used to seal adjacent layers. Layers can be assembled using adhesives in the following ways. A rigid contact adhesive (for example, 3M1151) can be used to join adjacent layers. A solvent release adhesive may be used to chemically bond two adjacent layers. An ultraviolet curing adhesive (for example, Loctite 3107) can be used to join adjacent layers when at least one layer is transparent in the ultraviolet. Precision applied epoxies, thermoset adhesives, and thermoplastic adhesives can also be used. Dry coatings that can be activated to bond using solvents, heat or mechanical compression can be applied to one or both surfaces. Layers can be welded together. For welding the layers preferably have similar glass transition temperatures and have mutual wetting and solubility characteristics. Layers can be welded using radio frequency dielectric heating, ultrasonic heating or local thermal heating.

The laminar flow channel can be straight or convoluted in any of a number of ways. In one embodiment, the flow channel can include a series of turns, making a stairstep or square wave geometry. Convoluted channels provide longer distances for diffusion to occur without increasing the size of the substrate plate in which the channel is formed.

The devices of this invention may comprise detecting means external to the channel for detecting the diffusion profile. Detection and analysis is done by any means known to the art, including optical means, such as optical spectroscopy, light scattering, and other means such as absorption spectroscopy or fluorescence, electrical means, e.g., electrodes inserted into the device, or virtually any microanalytical technique known to the art including magnetic resonance techniques, or other means known to the art to detect the diffusion profile. Preferably optical, fluorescent or chemiluminescent means are used. More preferably the labels used for the analyte particles are fluorescent and detection is done by means of a CCD camera or a scanning laser with a photomultiplier.

Computer processor means may be used to determine the presence or concentration of the analyte particles from the detected diffusion profile. The processor may be programmed to compare the diffusion profile with diffusion profiles taken using varying known concentrations of analyte, e.g., calibration curves or diffusion profiles in reference streams or to calculate analyte concentrations using algorithms described below.

The diffusion immunoassay method of this invention may be practiced as a continuous flow process, continuously monitoring analyte presence and/or concentration in a stream, or may be practiced in batch mode using small sample aliquots.

The concentration of binding particles in the diffusion fluid is preferably greater than or equal to the concentration of analyte particles in the analyte fluid, e.g., at least about one to about ten times greater. The analyte particles preferably encounter more binding particles than required. This can be adjusted to occur using flow rates and/or concentrations. High flow rates of the diffusion fluid will produce a narrower detectable band, and fewer binding particles are required.

As disclosed in the '213 patent, in its simplest form, a representative DIA uses a fluid containing sample antigen (SA) (also referred to herein as "analyte fluid") spiked with a known (predetermined) amount of labeled antigen (LA) (also referred to herein as "labeled analyte") placed in contact with a fluid containing a known concentration of antibody (Ab) (FIG. 1A) (also referred to herein as "diffusion fluid"). Two volumes of these fluids are placed into interdiffusive contact. The diffusion fluid contains a high molecular weight binding particle such as specific antibody (Ab). The analyte fluid contains at least one labeled conjugate of the antigen to be monitored (LA) and sample antigen (SA). It may also contain other diffusing and non-diffusing interferent compounds. FIG. 1B is a schematic representation of the concentration shown by detection of fluorescence of LA across the diffusion dimension at an early stage of diffusion for (free (LA), antibody-bound (AbLA), and total fluorescence (LA+AbLA)). LA and SA are much smaller and diffuse more rapidly than Ab. Here, the initial concentrations of Ab are much greater than LA+SA, allowing a significant fraction of LA and SA to bind. Bound antigen molecules diffuse much slower, resulting in an accumulation of signal near the fluid interface. FIG. 1C is a schematic representation of the case when Ab is much less than LA+SA. A small fraction of antigen molecules are able to bind due to the saturation of binding sites resulting in a diffusion profile more similar to that of free diffusion. Less LA accumulates near the fluid interface.

Over a given time interval, SA and LA "interdiffuse" with the Ab solution. Small antigen molecules (MW ~10 kD) will diffuse about 10-fold faster than large Ab molecules (MW ~150 kD). As LA and SA diffuse into the Ab solution, binding to Ab (creating either AbSA or AbLA) will significantly slow their diffusion. Thus the number of Ab binding sites relative to the concentration of total antigen will determine the distribution, or "diffusion profile," of antigen. Although the concentrations of LA and SA may be significantly different, the same fractions of LA and SA will be bound to Ab (assuming that the two species have similar diffusion and binding coefficients). Consequently, the diffusion profile of LA, the observed profile, is representative of the profile of total antigen. If the amount of Ab is much greater than the total labeled and unlabeled antigen, diffusion of LA will be maximally affected by binding events as shown in FIG. 1B resulting in an accumulation of LA shortly after diffusing into the Ab solution. If the amount of Ab is much less than the labeled and unlabeled antigen, the diffusion profile of LA will be less affected by binding events, as shown in FIG. 1C.

As discussed previously, in order for the above changes in the diffusion profile of the LA to be detectable, the AbLA complexes must have significantly different diffusion properties than the unbound LA particles. However, by using multivalent reactants (i.e., analyte and binding particles capable of binding with more than one binding and analyte particle, respectively), the DIAs of the present invention enable cross-linking between the AbLA complexes. Provided that the diffusion coefficient of these cross-linked aggregates are greater than that of the LA particles by an amount sufficient for the DIA response to be resolvable, the DIAs of the present invention allows for the diffusion coefficient of the non-aggregated complexes to be essentially the same as that of the analyte particles. As noted above, this expands the list of possible analytes to include classes of molecules which were not amenable to analysis by the DIA disclosed in the '213 patent.

As discussed in the Example below, laminar flow conditions and diffusion-dependent mixing achieved with a two-inlet T-Sensor were used to test the DIA concept of the present invention. The T-sensor concept is illustrated in FIG. 2A. At low Reynolds number conditions, preferably less than 1, the flows of the sample antigen (pre-mixed with labeled antigen) and the antibody solution run parallel to each other and do not mix except by diffusion. The concentration of a label such as a fluorophore can be monitored at any point downstream from the entry ports using a one- or two-dimensional detector array. If the device is relatively thin (in the w dimension), all components rapidly equilibrate along that axis and the problem can be treated using a one-spatial-dimensional analysis. If more than two streams are introduced into the device, it can be configured to include a reference or control material to provide a simultaneous one-point calibration of the device (see J. W. Paxton, F. J. Rowell, and J. G. Ratcliffe, *J. Immunol. Methods* 10, 317-27 (1976)).

FIG. 2A shows T-sensor 10 having diffusion stream inlet 12 leading into diffusion stream channel 14, and analyte stream 16 leading into analyte stream channel 18. These channels, 14 and 18, meet to form laminar flow channel 24, which ends in laminar flow channel outlet 28. Diffusion stream 20 and analyte stream 22 meet at inlet junction region 23 and flow together in laminar flow in laminar flow channel 24.

Two solutions, one containing Ab and referred to herein as diffusion stream 20, and the other containing both LA and SA, and referred to herein as analyte stream 22, are pumped into inlets 12 and 16 at equal, constant flow rates. Under low Reynolds number conditions, the flow streams run parallel to each other in the laminar flow channel 24 and do not mix except by diffusion. The midline 30 of laminar flow channel 24 is shown by a dotted line. Interdiffusion zone 32 on either side of midline 30 is the area in which analyte particles are diffusing into the left side of the laminar flow channel 24 and binding particles are diffusing into the right side of laminar flow channel 24.

Diffusion across the diffusion dimension (d-dimension) is dependent on time, which is controlled in the T-Sensor by flow rate and the traversed length (l) of the main channel. The diffusion profile along the d-dimension can be held at a steady state at any distance l by maintaining the flow rate, allowing continuous monitoring of the diffusion profile using one- or two-dimensional detector arrays. To infer the concentration of SA, the concentration profile of LA across the d-dimension of the main channel is measured at an appropriate distance l along laminar flow channel 24 at detection zone 26. At inlet junction region 23 of the two streams, there is a flow development region in which the flow velocity is less than that in the fully developed flow downstream. We ignore this effect in analytical modeling because it is insignificant at greater than about 1 mm downstream where measurement occurs. In this Figure, the y coordinate indicates the length dimension (l), the z coordinate indicates the diffusion dimension or depth (d), and the x coordinate indicates the width dimension (w).

Figure 2B:
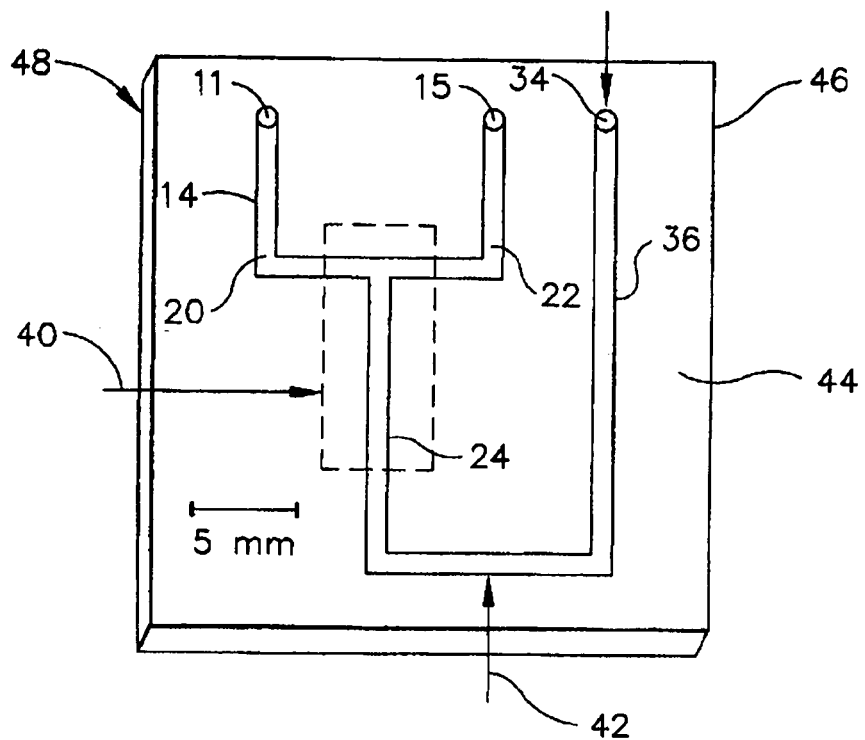
FIG. 2B shows further aspects of the device.

A representative T-Sensor device is further shown in FIG. 2B. The device illustrated utilizes top glass cover slip 44 and bottom glass cover slip 46. In top glass cover slip 44, three round holes or ports, diffusion stream inlet port 11, analyte stream inlet port 15, and drain port 34, are drilled for access respectively to the diffusion stream channel 14, analyte stream channel 18, and drain channel 36. Between cover slips 44 and 46 is a piece of 100 μm thick Mylar chip 48 coated on both sides with adhesive (Fraylock, Inc., San Carlos, Calif.), through which the channels were cut using a carbon dioxide laser cutting system (Universal Laser Systems). The laminar flow channel 24 is 750 μm wide in the d-dimension (scale bar=5 mm).

Figure 2C:
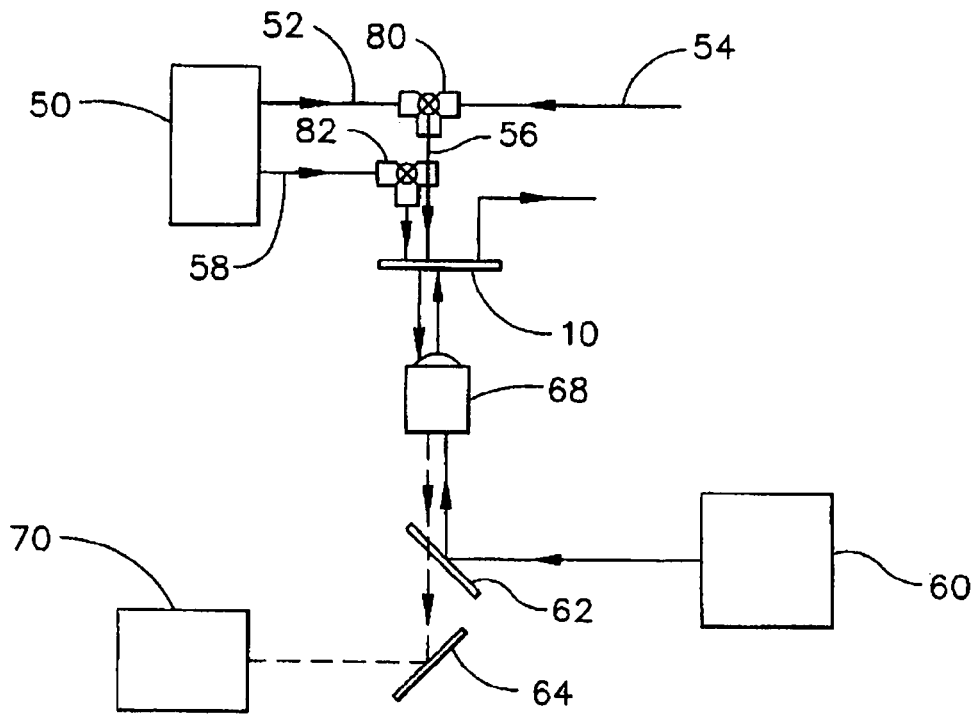
FIG. 2C is a block diagram of a representative apparatus employed to acquire data from the diffusion immunoassay of FIGS. 2A and 2B.

FIG. 2C is a block diagram of a representative apparatus employed to acquire data from the diffusion immunoassay of FIGS. 2A and 2B. Reagents were manually loaded into the fluid lines (polyetheretherketone tubing, Upchurch Scientific) and then pushed through the device using a Kloehn syringe pump 50. Sample analyte conduit 52 contains the sample fluid. Labeled analyte conduit 54 contains labeled analyte to be mixed with the sample fluid containing sample antigen and flows into analyte conduit 56 through analyte valve 80. Labeled analyte particles (fluorescein-labeled antigen) flowing through the laminar flow channel of the T-Sensor 10 were excited using a 50 W halogen lamp (Zeiss) 60 and the emission signal was magnified six times by a Zeiss microscope 68 and captured using an integrating charge coupled device (CCD) camera (Retiga 1300, Q-Imaging, Burnaby, BC, Canada) 70. Light from lamp 60 of a wavelength capable of being reflected by dichroic mirror 62, passes through microscope 68 and is reflected from T-sensor 10. The reflected light, having wavelengths determined by labeled analyte particles in T-sensor 10, now passes through dichroic mirror 62 and is reflected from mirror 64 to the CCD camera 70.

EXAMPLE

The microscale diffusion immunoassay of this invention was demonstrated using a model system with a heterotetrameric mouse immunoglobulin G (MsIgG) as the analyte particle, and a goat derived antibody specific to mouse immunoglobulin G ($\alpha$-MsIgG) as the binding particle. Because MsIgG is multimeric, it has at least two identical epitopes that are recognized by the bivalent $\alpha$-MsIgG, and, thus, the system meets the criteria for cross-linking of antibody/antigen complexes. The specific assay format employed utilized a diffusion interface created by constant laminar flow in a T-sensor, with $\alpha$-MsIgG in one flow stream and a mixture of labeled and unlabeled MsIgG in the other flow stream. This resulted in a competitive DIA with two reagents (one of which is premixed with the sample or unknown).

Solutions

The MsIgG was obtained in both unlabeled and fluorescein-labeled (FITC-MsIgG) versions from a commercial vendor (Sigma Chemicals, St. Louis, Mo., USA). The $\alpha$-MsIgG (Chemicon International, Temecula, Calif., USA) was diluted from the stock solution to a concentration of 381.5 nM (or a concentration of binding sites of 683 nM) with 100 mM HEPES buffer, pH 7.0 (Sigma Chemicals, St. Louis, Mo., USA) amended with 1 mg/mL bovine serum albumin (Sigma Chemicals, St. Louis, Mo., USA) to prevent non-specific adsorption to the device surfaces. Numerous mock sample/reagent solutions were made with a constant concentration of FITC-MsIgG (25 nM) mixed with MsIgG to final concentrations spanning the expected dynamic range (0-1500 nM MsIgG), using the same amended buffer used to dilute the antibody.

Device

A T-sensor with the dimensions l=40 mm, d=1.6 mm, and w=0.10 mm was used to perform the experiments. This device was a three-layer plastic laminate—the flow channel was cut out of a 0.10 mm thick layer of Mylar D coated on both sides with adhesive (Fralock, Santa Clara, Calif., USA), inlet holes were cut through a 0.175 mm thick capping layer of Rohaglas #99524 PMMA (Cyro Industries, Orange, N.J., USA), and a second Rohaglas capping layer sealed the device.

Procedure

A typical DIA procedure was used. Syringe pumps (Kloehn, Las Vegas, Nev., USA) were used to precisely pump the $\alpha$-MsIgG reagent into one inlet of the T-sensor and the mock sample/labeled analyte reagent solutions into the other. Both inlets were pumped at 21 nLs$^{-1}$, for a total flow rate of 42 nLs$^{-1}$, resulting in a 154 s interaction time before detection. Sufficient volumes of solutions were used to result in a constant concentration feed solution for the duration of the experiment (~300 mL). Ten replicate images with a cooled, 12-bit Retiga CCD camera (Q-Imaging, Burnaby, BC, Canada) were taken over a 5 minute period after the establishment of constant flow. The diffusion profile at the detection zone was determined, and the ten profiles were averaged. This average was then corrected for background (using images of buffer) and flatfield (using images of a uniform field of 25 nM FITC-MsIgG solution). The diffusion profiles were normalized to the extremes of the profiles where the DIA response is not expected to differ from solution to solution. They were also numerically noise-filtered with a Whittaker smoother (see P. H. C. Eilers, *Anal. Chem.*, 75, 3631-3636 (2003)), and a central-difference (see J. H. Mathews, *Numerical methods using MATLAB*, 3$^{rd}$ Ed., Prentice Hall, Upper Saddle River, N.J. (1999)) was calculated to yield a numerical approximation of the first-derivative. Finally, a univariate abstraction of the response was done in the same manner as in the phenyloin DIA of the '213 patent (see also A. Hatch, A. E. Kamholz, K. R. Hawkins, M. S. Munson, E. A. Schilling, B. H. Weigl and P. Yager, *Nature Biotech.*, 19, 461-465 (2001)). Multiple replicates of these univariate response values were subjected to ANCOVA analysis to determine if the response was significant (see R. O. Kuehl, *Design of Experiments: Statistical Principles of Research Design and Analysis*, 2$^{nd}$ Ed., Duxbury/Thomson Learning, Pacific Grove, Calif. (2000)) and significantly modulated by the changing concentrations of the mock samples over the range assayed. A log/logit data transformation (see R. J. Maciel, *J. Clin. Immunoassay*, 8, 98-106 (1985)) was used to stabilize the variances and linearize the DIA response for the ANCOVA. This transformation was chosen because the phenyloin DIA response of the '213 patent modeled by a four-parameter log/logit standard curve displayed good correlation in sample quantification with an established reference method (see A. Hatch et al. supra).

Results

Figure 3A:
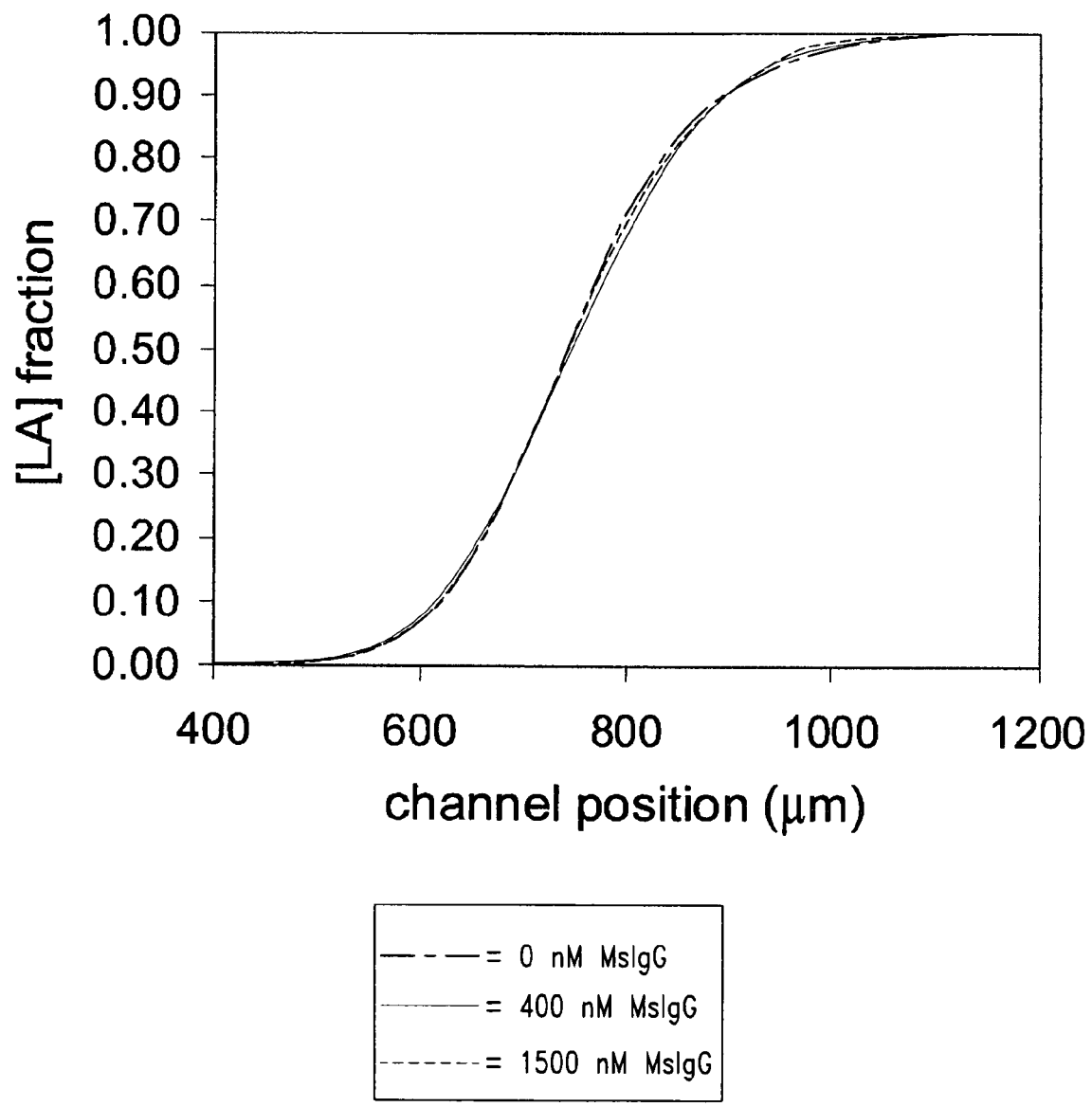
FIG. 3A shows predicted accumulation profiles assuming that a simple complex of analyte and binding particles (i.e., one MsIgG per α-MsIgG) is the only type of complex formed.
Figure 3B:
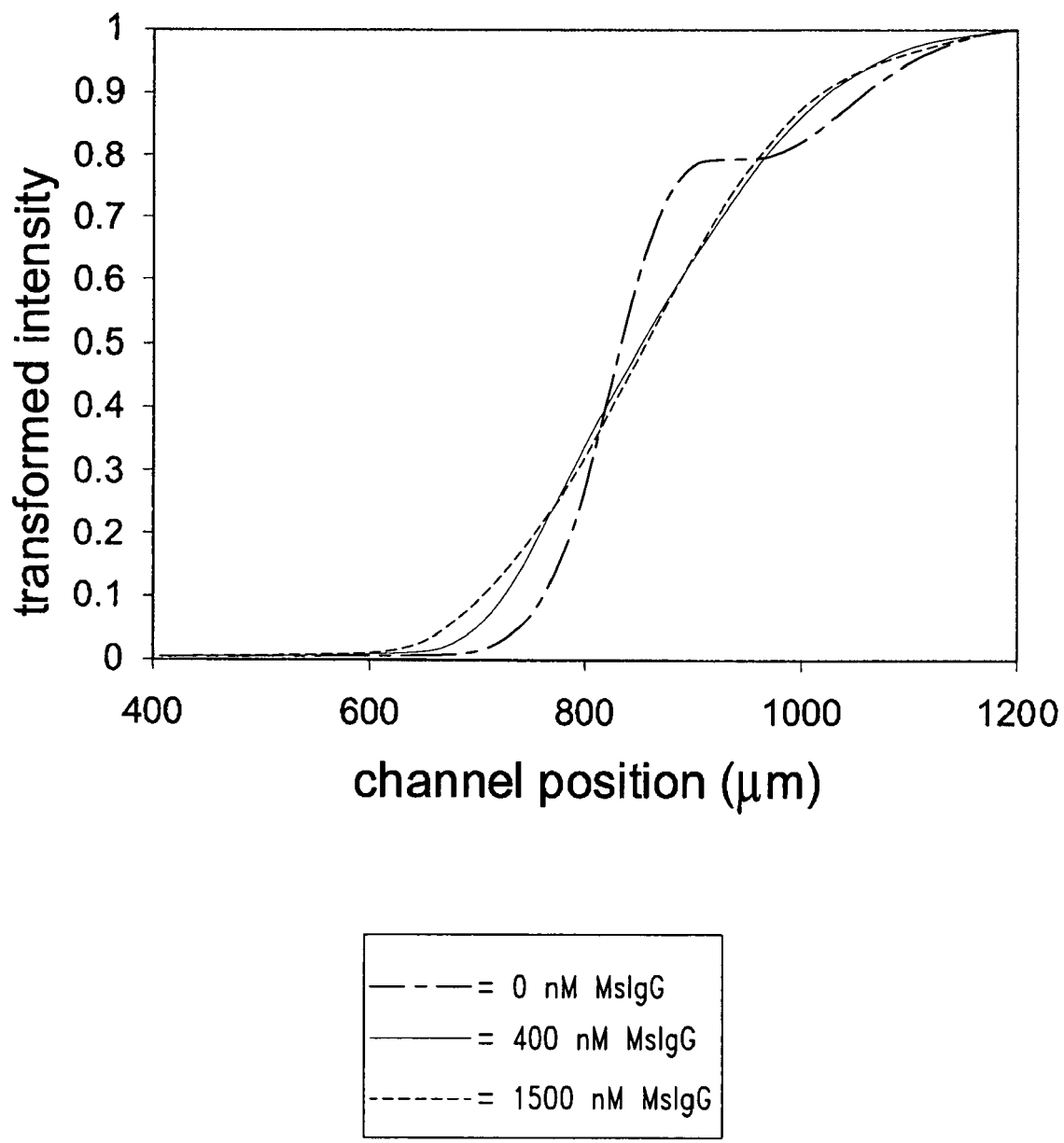
FIG. 3B shows observed accumulation profiles.

An obvious DIA response was apparent with this assay system. As shown in FIG. 3A, which shows the predicted accumulation profiles assuming a simple complex formed from one MsIgG per $\alpha$-MsIgG, this result was not predicted by simulations assuming no cross-linking. However, FIG. 3B, which shows the observed accumulations, evidences that the DIA response was modulated by changing MsIgG concentration. Alternative hypotheses for the source of this response (experimental artifact or adsorption of FITC-MsIgG to device surfaces) were eliminated by appropriate control experiments (data not shown) and extensive replication.

Figure 4A:
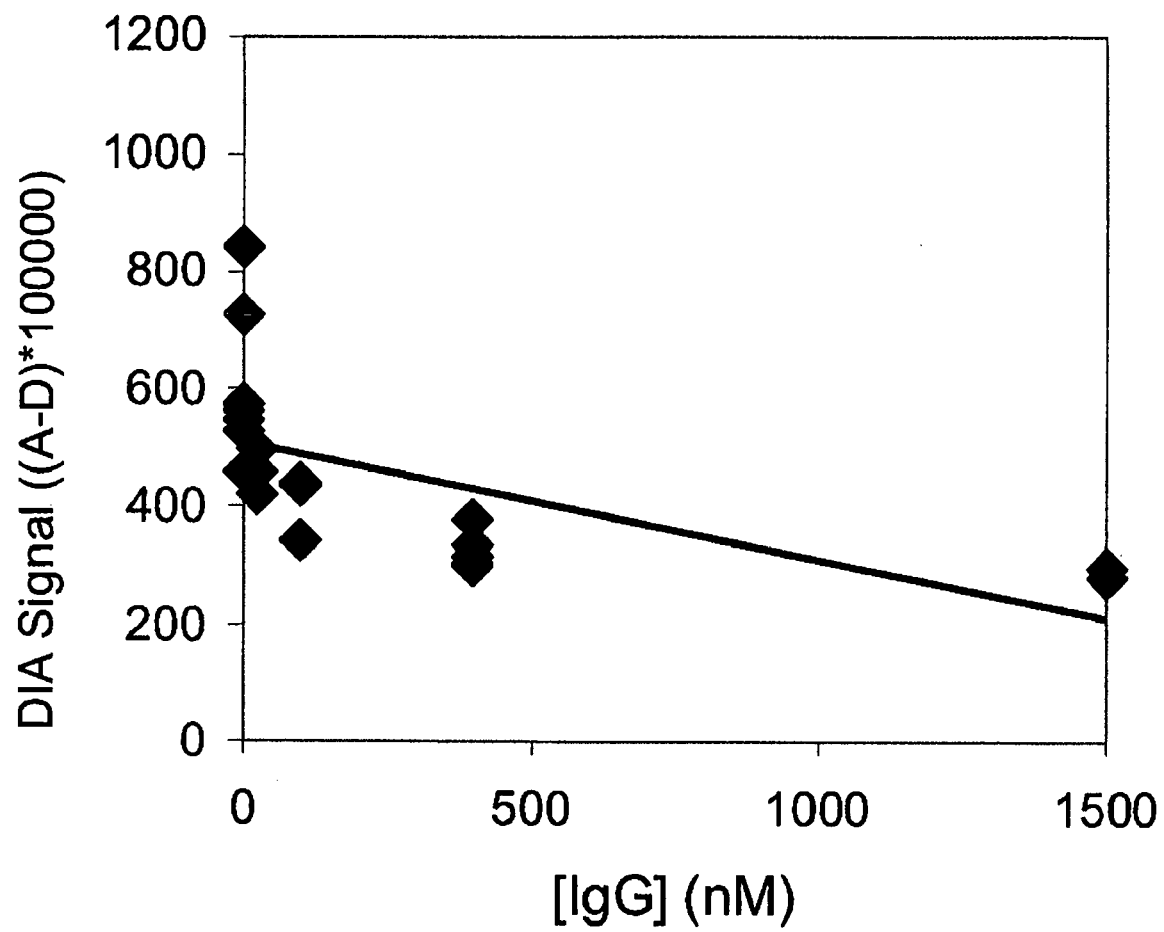
FIGS. 4A-4C show plots of the response (scaled or transformed for ANCOVA analysis) versus concentration of MsIgG, with fitted linear covariance model for a diffusion immunoassay of the present invention.
Figure 4B:
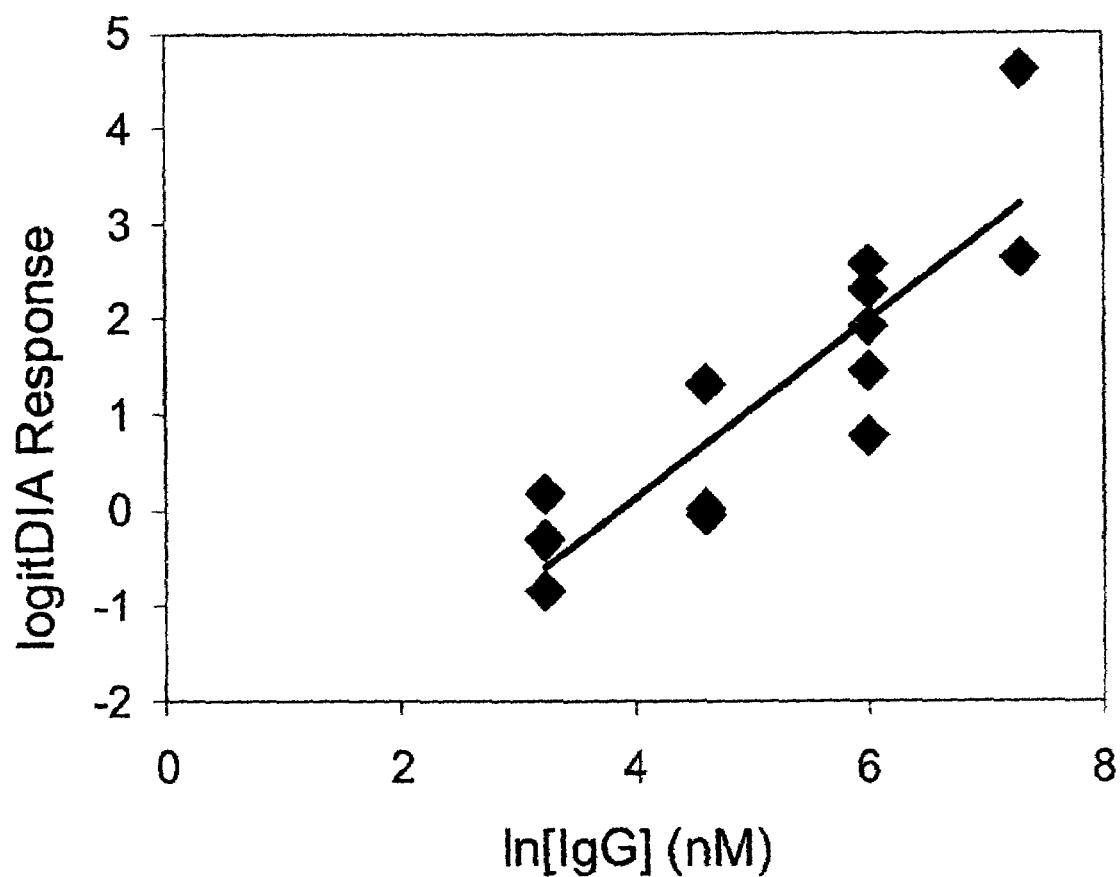
Figure 4C:
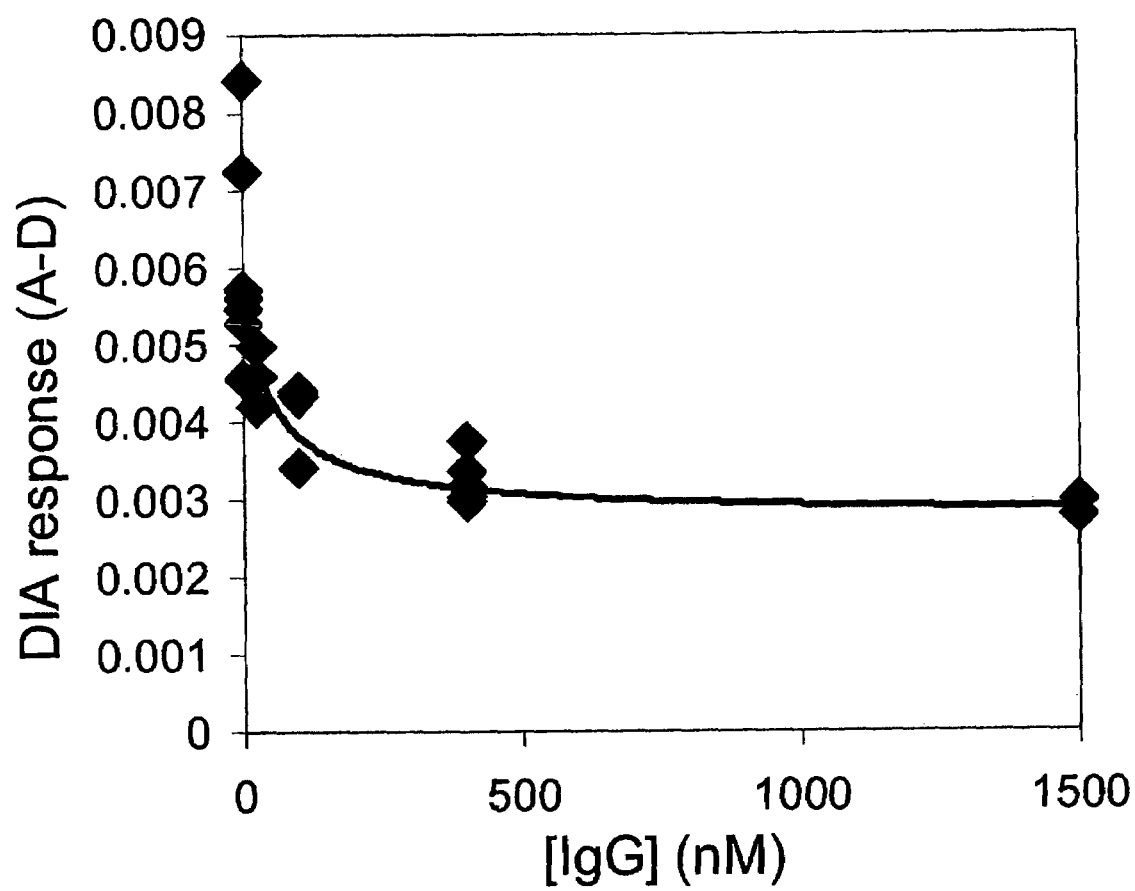

As shown in FIGS. 4A-C, the ANCOVA analysis shows that the observed response is significant, namely, that the differences in DIA response between solutions having different MsIgG concentration is not explainable by the observed random variation within the replicates of single solution, and are well described by the log/logit model. FIG. 4A shows the scaled data without transformation. ANCOVA analysis for this data set implies significant variation ($P_r$>F=0.003) for a fitted model (y=−0.20x+507). FIG. 4B shows the data of FIG. 4A (without scaling of y) transformed by a log/logit transformation (x'=ln(x);y'=ln[y$_0$−y)/(y−y$_\alpha$)]. ANCOVA analysis for this data set implies highly significant variation ($P_r$>F<0.0001) for a fitted model (y=0.93x−3.57). FIG. 4C shows the fitted log/logit relationship from FIG. 4B plotted on untransformed axes to show the fir to the data that was absent in FIG. 4A.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. For example, the '213 patent discloses a number of other microscale diffusion immunoassay methods and systems beyond those embodiments specifically discussed above, and, as one of ordinary skill in the art will appreciate, the use of multivalent reactants may also be advantageously utilized in such methods and systems. Accordingly, the invention is not limited except as by the appended claims.

The invention claimed is:

1. A method for detecting the presence of analyte particles in an analyte fluid comprising:
   (a) providing the analyte fluid comprising the analyte particles;
   (b) providing a diffusion fluid comprising binding particles capable of binding with the analyte particles;
   (c) flowing the analyte fluid and the diffusion fluid in adjacent laminar flow through a microfluidic channel;
   (d) allowing the analyte particles to diffuse into the diffusion fluid and bind with the binding particles to form analyte/binding particle complexes;
   (e) allowing the analyte/binding particle complexes to cross-link to form cross-linked aggregates; and
   (f) detecting the presence of the analyte particles and the cross-linked aggregates,
   wherein:
   each of the binding particles is capable of binding with more than one analyte particle;
   each of the analyte particles is capable of binding with more than one binding particle;
   the non-aggregated analyte/binding particle complexes and the analyte particles are at least the same order of magnitude in size and have diffusion coefficients that are essentially the same; and
   the cross-linked aggregates have a diffusion coefficient that is at least two times greater than the diffusion coefficients of the non-aggregated analyte/binding particle complexes and the analyte particles.

2. The method of claim 1, further comprising:
   (g) detecting a diffusion profile in the microfluidic channel formed by the analyte particles and the cross-linked aggregates; and
   (h) determining the concentration of the analyte particles.

3. The method of claim 2 wherein the concentration of analyte particles is determined based upon the diffusion profile of the analyte particles and cross-linked aggregates complexes.

4. The method of claim 2 wherein the concentration of analyte particles is determined by comparing the diffusion profile to a calibration profile.

5. The method of claim 1 wherein at least one of the analyte particles is labeled with a detectable marker.

6. The method of claim 1 wherein at least one of the binding particles is labeled with a detectable marker.

7. The method of claim 1 wherein the binding particles are antibodies.

* * * * *

UNITED STATES PATENT AND TRADEMARK OFFICE
CERTIFICATE OF CORRECTION

PATENT NO. : 7,550,267 B2  
APPLICATION NO. : 11/226054  
DATED : June 23, 2009  
INVENTOR(S) : Hawkins et al.

Page 1 of 1

It is certified that error appears in the above-identified patent and that said Letters Patent is hereby corrected as shown below:

On the title page, item [56] Page 2, under the heading "U.S. Patent Documents" insert --5,869,620 A * 2/1999 Whitlow et al....530/387.3--

Signed and Sealed this

Eleventh Day of August, 2009

David J. Kappos  
*Director of the United States Patent and Trademark Office*